United States Patent [19]

Wilson et al.

[11] 4,172,133

[45] Oct. 23, 1979

[54] (1,4)DITHIINO (2,3-b)(1,3)THIAZOLE-(4,5-e) PYRAZINE-6,7-DICARBONITRILES

[75] Inventors: Charles A. Wilson; Craig E. Mixan, both of Midland, Mich.

[73] Assignee: The Dow Chemical Company, Midland, Mich.

[21] Appl. No.: 955,287

[22] Filed: Oct. 27, 1978

[51] Int. Cl.$^2$ .................... C07D 495/14; A01N 9/12
[52] U.S. Cl. ..................................... 424/250; 544/345
[58] Field of Search ......................... 544/345; 424/250

[56] References Cited

U.S. PATENT DOCUMENTS

| | | | |
|---|---|---|---|
| 3,761,475 | 9/1973 | Kurihara et al. | 544/345 |
| 4,075,204 | 2/1978 | Wilson et al. | 544/345 |
| 4,075,207 | 2/1978 | Tong | 424/250 |

*Primary Examiner*—Paul M. Coughlan, Jr.

[57] ABSTRACT

Novel (1,4)Dithiino(2,3-b)(1,3)thiazole-(4,5-e)pyrazine-6,7-dicarbonitriles, their method of use in the control and kill of bacteria and fungi, and compositions containing the novel compounds as the active ingredients therein are claimed.

4 Claims, No Drawings

(1,4)DITHIINO(2,3-b)(1,3)THIAZOLE-(4,5-e)PYRAZINE-6,7-DICARBONITRILES

SUMMARY OF THE INVENTION

This invention concerns novel (1,4)Dithiino(2,3-b)(1,3)thiazole(4,5-e)pyrazine-6,7-dicarbonitriles, hereinafter alternatively referred to as "active compounds," corresponding to the formula

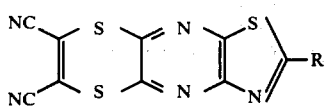

wherein R is —H or —CH₃.

The active compounds directly or as the active ingredients in formulations and compositions, exhibit, in antimicrobially-effective amounts, antimicrobial activity against fungi and bacteria. Hereinafter the terms "antimicrobial" and "antimicrobially-effective," when used in conjunction with the active compounds, will be employed to identify their activity against fungi and bacteria.

The active compounds are prepared by adding the appropriate 5,6-dichlorothiazole(4,5-b)pyrazine to disodium dimercaptomaleonitrile in dimethylformamide (DMF) in accordance with the following equation:

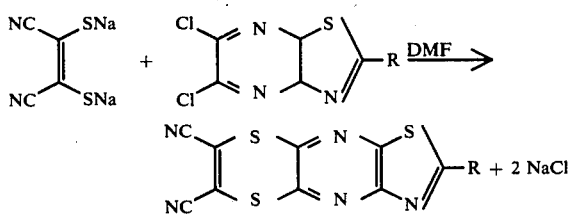

wherein R is as previously defined.

The reaction mixture is maintained at about 10° C. to about 50° C., and preferably from about 20° C. to about 40° C., with agitation until substantial completion of the reaction; usually from about ½ to about 2 hours. Upon completion of the reaction, the resulting product mass is poured into ice water and allowed to stand for from about one to about three days, during which time the desired crude solid product precipitates. The product compound may be purified by conventional techniques known to those skilled in the art.

Ordinarily substantial equimolar proportions of the starting materials are employed in the above-described process. However, any of the starting materials can be used in excess of the equimolar stoichiometric requirement.

DESCRIPTION OF THE PREFERRED EMBODIMENTS

The following example and teachings illustrate the present invention and the manner by which it can be practiced but as such should not be construed as limitations upon the overall scope of the same. The product compound is identified by elemental analysis, nuclear magnetic resonance spectroscopy, and infrared spectroscopy.

EXAMPLE—Preparation of (1,4)Dithiino(2,3-b)(1,3)thiazole(4,5-e)pyrazine-6,7-dicarbonitrile (Example Compound)

To a stirred solution of 5 g (0.025 mole) disodium dimercaptomaleonitrile in 150 ml of dimethylformamide was added 5 g (0.025 mole) of 5,6-dichlorothiazole(4,5-b)pyrazine. The reaction mixture was stirred at 40° C. for 1 hour and was thereafter poured into 500 ml of ice water. The reaction mixture was allowed to stand for two days. The resulting light tan solid precipitate was collected by suction filtration, dried, dissolved in a benzene/methylene chloride solution and eluted through a 10 cm silica gel column. The eluent was evaporated to dryness under reduced pressure, recrystallized from benzene/hexane and dried in vacuo to yield 2.5 g of a yellow solid (a 36% yield, calculated from the thiazole pyrazine) m.p. 192°–195° C. (decomposition).

A sample was subjected to elemental analysis. The results obtained were as follows:

Analysis for $C_9HN_5S_3$: Calcd.: C, 39.26; N, 25.44; H, 0.37. Found: C, 39.8; N, 24.82; H, 0.68.

The active compounds of the invention are useful as antimicrobials for the control of bacteria and fungi. This is not to suggest that the active compounds and mixtures thereof with usual additives are equally effective against all such organisms at the same concentration. For such uses, the active compounds can be employed in an unmodified form or dispersed on a finely divided solid and employed as a dust. Such mixtures can also be dispersed in water with the aid of a surface-active agent and the resulting emulsion employed as a spray. In other procedures, the active compounds can be employed as the active constituent in solvent solutions, oil-in-water or water-in-oil emulsions. The augmented compositions are adapted to be formulated as concentrates and subsequently diluted with additional liquid or solid adjuvants to produce the ultimate treating compositions. Good control and kill have been realized against a number of representative compositions wherein antimicrobially-effective amounts of from about 0.5 to about 500 parts by weight of an active compound per million parts of such compositions are employed. As stated hereinbefore the active antimicrobially-effective amount to be employed against a given organism or in a certain composition can readily be determined by one skilled in the art.

Incorporation of the active compounds of this invention into materials which are subject to fungal attack inhibits the growth of the fungi and preserves the original value of the materials. The compounds is sufficiently nonvolatile and water-insoluble that it will persist on or in such materials for long periods of time. Examples of materials which are adversely affected by fungal growth are latex and alkyl paint films, wood and wooden products. The active compounds are sufficiently active against fungi such that only small quantities are required to prevent mildew on paint films or wood rot. The active compounds are therefore useful for long-term protection against fungal growth in or on materials having a wood basis or a protective or decorative paint film subject to fungal attack.

In representative activity tests, a predetermined amount of the Example compound is dispersed in warm melted nutrient agar which is then poured into a petri dish and allowed to solidify, the active compound being employed in an amount sufficient to provide from 0.5 to 500 parts by weight thereof per million parts (ppm) of the ultimate agar composition. The surface of the agar is then inoculated with a variety of bacterial and fungal pest organisms, and the inoculated plates are incubated under conditions conducive to bacterial and fungal growth.

In these studies, the compound of the Example gave 100% growth inhibition (kills) and control of the following organisms at the indicated concentrations in parts per million:

TABLE

Antimicrobial Activity of (1,4)Dithiino(2,3-b)-
(1,3)thiazole(4,5-e)pyrazine-6,7-dicarbonitrile

| Organism | Concentration in ppm |
| --- | --- |
| S. aureus | 5 |
| S. typhosa | 10 |
| B. subtilis | 5 |
| S. marcesens NIH | 50 |
| E. coli ATCC 11229 | 100 |
| C. albicans N | 0.5 |
| C. albicans D | 1 |
| C. pelliculosa | 1 |
| T. specie med. col. VI | 1 |
| A. pullulans | 5 |
| C. ips | 1 |
| T. mentagrophytes | 0.5 |
| P. chrysogesum | 1 |
| Trichoderm Sp. P-42 | 5 |
| A. fumigatus | 0.5 |

TABLE-continued

Antimicrobial Activity of (1,4)Dithiino(2,3-b)-
(1,3)thiazole(4,5-e)pyrazine-6,7-dicarbonitrile

| Organism | Concentration in ppm |
| --- | --- |
| A. niger | 1 |

Preparation of the Starting Material

The thiazolopyrazine starting materials are disclosed in and can be prepared according to the process taught in Tong, U.S. Pat. No. 4,075,207.

What is claimed is:

1. A compound of the formula

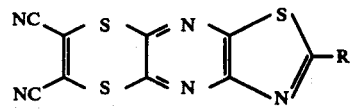

wherein R is —H or —CH$_3$.

2. The compound of claim 1 which is (1,4)Dithiino-(2,3-b)(1,3)thiazole(4,5-e)pyrazine-6,7-dicarbonitrile.

3. A method for controlling bacteria and fungi which comprises applying to said bacteria and fungi or their habitat an antimicrobially-effective amount of the compound of claim 1.

4. A composition for controlling bacteria and fungi comprising an antimicrobially-effective amount of the compound of claim 1 in combination with a solid or liquid diluent medium.

* * * * *